US009533304B2

(12) United States Patent
Davies et al.

(10) Patent No.: US 9,533,304 B2
(45) Date of Patent: Jan. 3, 2017

(54) FORMING SAMPLE COMBINATIONS USING LIQUID BRIDGE SYSTEMS

(71) Applicant: Stokes Bio Limited, Limerick (IE)

(72) Inventors: Mark Davies, Limerick (IE); Tara Dalton, Limerick (IE)

(73) Assignee: STOKES BIO LIMITED, Shannon Arms, Limerick (IE)

(*) Notice: Subject to any disclaimer, the term of this patent is extended or adjusted under 35 U.S.C. 154(b) by 116 days.

(21) Appl. No.: 13/960,720

(22) Filed: Aug. 6, 2013

(65) Prior Publication Data

US 2014/0038196 A1 Feb. 6, 2014

Related U.S. Application Data

(63) Continuation of application No. 12/469,325, filed on May 20, 2009, now Pat. No. 8,501,497, which is a (Continued)

(51) Int. Cl.

*G01N 33/544* (2006.01)
*B01L 3/00* (2006.01)
(Continued)

(52) U.S. Cl.

CPC .......... *B01L 3/5025* (2013.01); *B01F 13/0071* (2013.01); *B01L 3/502715* (2013.01); *B01L 3/502784* (2013.01); *B01L 7/525* (2013.01); *C40B 50/08* (2013.01); *C40B 60/14* (2013.01); *B01J 2219/00599* (2013.01); *B01J 2219/00722* (2013.01); *B01J 2219/00889* (2013.01); *B01L 7/52* (2013.01); *B01L 2200/027* (2013.01); *B01L 2200/0605* (2013.01); *B01L 2200/0673* (2013.01); *B01L 2300/0819* (2013.01); *B01L 2300/0838* (2013.01); *B01L 2300/0867* (2013.01); *B01L 2300/1805* (2013.01); *B01L 2400/0406* (2013.01); *B01L 2400/0487* (2013.01); *B01L 2400/0688* (2013.01); *G01N 2035/00544* (2013.01)

(58) Field of Classification Search

CPC .............................. G01N 35/08; G01N 33/544
See application file for complete search history.

(56) References Cited

U.S. PATENT DOCUMENTS 6,193,471 B1 2/2001 Paul
7,235,405 B2 6/2007 Charles et al.
(Continued)

FOREIGN PATENT DOCUMENTS

EP 1574586 9/2005
EP 1361442 7/2006
(Continued)

OTHER PUBLICATIONS

PCT/IE2007/000013, Written Opinion of the Inerrnational Searching Authority, 8 Pgs.
(Continued)

*Primary Examiner* — Jyoti Nagpaul
(74) *Attorney, Agent, or Firm* — Jones Robb, PLLC

(57) ABSTRACT

The present invention generally relates to methods of constructing liquid bridges and methods of forming predetermined combinations of samples using liquid bridges.

8 Claims, 13 Drawing Sheets

Related U.S. Application Data continuation-in-part of application No. 12/092,261, filed as application No. PCT/IE2007/000013 on Feb. 7, 2007, now Pat. No. 8,298,833.

(60) Provisional application No. 60/765,671, filed on Feb. 7, 2006.

(51) Int. Cl.

| | |
|---|---|
| ***B01F 13/00*** | (2006.01) |
| ***C40B 50/08*** | (2006.01) |
| ***C40B 60/14*** | (2006.01) |
| *B01L 7/00* | (2006.01) |
| *G01N 35/00* | (2006.01) |

(56) References Cited

U.S. PATENT DOCUMENTS

| | | | | |
|---|---|---|---|---|
| 2002/0182749 | A1 | 12/2002 | Singh et al. | |
| 2003/0080143 | A1* | 5/2003 | Kale | B01L 3/0262 222/1 |
| 2003/0182729 | A1 | 10/2003 | Williams | |
| 2004/0022686 | A1* | 2/2004 | Charles et al. | 422/82.08 |
| 2006/0094119 | A1 | 5/2006 | Ismagilov et al. | |
| 2006/0257893 | A1 | 11/2006 | Takahashi et al. | |
| 2007/0275415 | A1 | 11/2007 | Srinivasan et al. | |
| 2008/0277494 | A1 | 11/2008 | Davies et al. | |
| 2010/0216128 | A1 | 8/2010 | Davies et al. | |

FOREIGN PATENT DOCUMENTS

| | | | |
|---|---|---|---|
| WO | 2001/01106 | | 4/2001 |
| WO | 2007/091228 | A1 | 8/2007 |
| WO | 2007/091229 | A1 | 8/2007 |
| WO | 2007/091230 | A1 | 8/2007 |
| WO | 2010/133962 | | 11/2010 |
| WO | 2010/133963 | A3 | 11/2010 |

OTHER PUBLICATIONS

PCTIB2010/001233, International Search Report mailed on Oct. 22, 2010, 10 Pgs.

EPC Communication Pursuant to Article 94(3) for Application No. 10 749 681.2 dated May 17, 2016.

International Search Report for Applicaton No. PCT/IB2010/001254 dated Nov. 25, 2010.

International Search Report for Application No. PCT/IE2007/000013 dated May 11, 2007.

* cited by examiner (A) (B) (C) (D)

Dimensionless plot of dimensionless plug volume, $V^*$, versus slenderness ratio, where $\Lambda^*$ was $V^*$ scaled with $R_2^3$. Results are plotted for $K^*$ values of 1.0, 0.44 and 0.25.

Liquid bridge dispensing at three different values capillary radii ratio, $K^*$. (A) $K^* = 0.25$ (B) $K^* = 0.44$ and (C) $K^* = 1.0$ Capillary tip separations are indicated on the images.

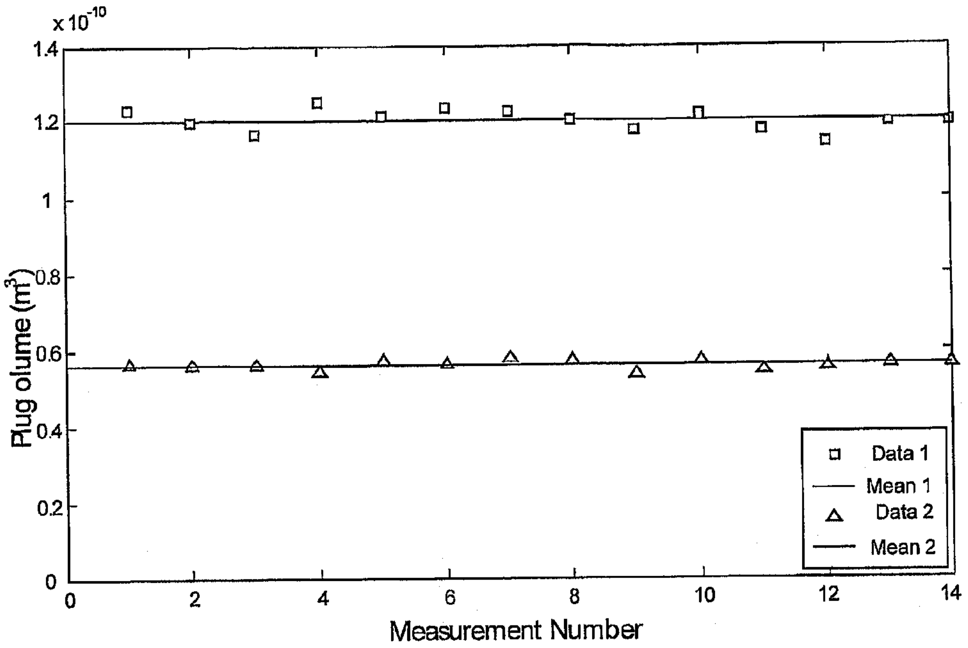

Plug volume variation over fourteen measurements for . $K^* = 0.44$ Horizontal lines represent the mean volume dispensed. The mean plug volumes were approximately 120 nL and 56 nL with maximum variations ±4.46% of and ±3.53% respectively.

FIG. 14

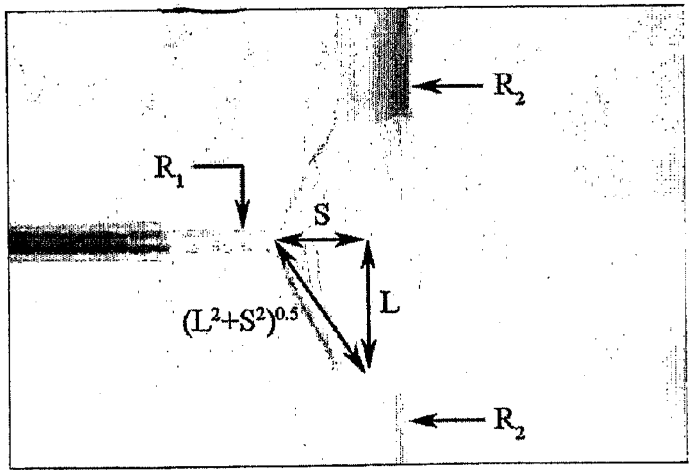

Funicular liquid bridge supported between three capillaries. The geometry used to investigate stability is shown superimposed over the original image.

FIG. 15

Experimentally determined stability diagram for a purified water funicular liquid bridge in a density matched silicone oil, Bond number: 1.25 x $10^{-4}$ .Vertical error bars indicate the volumetric ratio uncertainty as a result of camera frame rate.

FORMING SAMPLE COMBINATIONS USING LIQUID BRIDGE SYSTEMS

RELATED APPLICATIONS

The present invention is a continuation-in-part of U.S. nonprovisional patent application Ser. No. 12/092,261, filed Apr. 30, 2008, which is a U.S. national phase patent application from PCT international patent application number PCT/IE2007/000013, filed Feb. 7, 2007, which claims priority to U.S. provisional patent application Ser. No. 60/765,671, filed Feb. 6, 2007, each of which is incorporated by reference herein in its entirety.

FIELD OF INVENTION

The present invention generally relates to methods of constructing liquid bridge systems and methods of forming predetermined combinations of samples using liquid bridge systems.

BACKGROUND

Microfluidics involves micro-scale devices that handle small volumes of fluids. Because microfluidics can accurately and reproducibly control and dispense small fluid volumes, in particular volumes less than 1 μl, application of microfluidics provides significant cost-savings. The use of microfluidics technology reduces cycle times, shortens time-to-results, and increases throughput. Furthermore, incorporation of microfluidics technology enhances system integration and automation.

Given the small dimensions of microfluidic devices or components thereof, these devices involve construction and design that differs from macro-scale devices. Simple scaling down in size of conventional scale devices to a microfluidic scale is not a design option. For example, liquid flow in microfluidic devices differs from that of macro-scale size devices. Because liquid flow tends to be laminar, surface flux and surface tension start to dominate and as a result, effects not seen at the macro level become significant at the microfluidic level. Other differences at the microfluidic level include faster thermal diffusion, predominately laminar flow, and surface forces that are responsible for capillary phenomena.

There is an unmet need for improved microfluidic devices and systems and methods of generating microfluidic samples.

SUMMARY

The invention generally relates to methods of using liquid bridges in order to facilitate mixing multiple samples. A liquid bridge is a device in which liquid droplets containing a sample of interest are formed. The droplets formed in a liquid bridge are enveloped in an immiscible carrier fluid. A typical liquid bridge of the invention is formed by an inlet in communication with a chamber that is filled with a carrier fluid. The carrier fluid is immiscible with sample droplets flowing through the inlet into the chamber. The sample droplet expands until it is large enough to span a gap between the inlet and an outlet in communication with the chamber. Droplet formation is accomplished in many ways, for example, by adjusting flow rate or by joining a second sample droplet to the first sample droplet, resulting in formation of an unstable funicular bridge that subsequently ruptures from the inlet. After rupturing from the inlet, the sample droplet enters the outlet, surrounded by the carrier fluid from the chamber.

The invention provides methods of using liquid bridges in order to create a sample array that allows mixing of a predetermined number of different samples. The invention provides methods for constructing a liquid bridge system having a predetermined number of liquid bridges sufficient for matrix combinations of any number of samples. Ina preferred embodiment, a first sample array is combined with a second sample array. Aspects of the invention are accomplished by ascertaining a number of wells within the first array of samples, and ascertaining a number of wells within the second array of samples. For example, the first array and the second array may each independently be a 96 well plate or a 384 well plate. The first array and the second array may each independently be an array having any number of wells (e.g., from about 2 to about 5000).

Based on the number of wells in each of the first and second sample array, a formula $a_n \times b_n$ is applied, in which $a_n$ is the number of wells in the first array and $b_n$ is the number of wells in the second array. The output of this formula determines the number of liquid bridges needed to combine a first sample array and a second sample array to obtain the desired number of sample combinations. For example, if a first array has four wells and a second array has four wells, then a system would be constructed having 16 liquid bridges. Alternatively if a first array has twelve wells and a second array has twelve wells, then a system would be constructed having 144 liquid bridges. Not all of the wells of each array are required to be filled with a sample. For example, at least one of the sample combinations can be a combination of a blank from the first array and a blank from the second array. An exemplary blank is oil, e.g., silicone oil.

The first and second array of samples can each independently be chemical or biological species. For example, the first array of samples can be primers for PCR reactions and the second array of samples can include nucleic acid (e.g., DNA or cDNA) from a biological sample to be amplified by PCR.

In another aspect, the invention provides a method for forming predetermined sample combinations including, providing a first sample array, providing a second sample array, and providing at least one liquid bridge to mix the first sample array with the second sample array, wherein the number of liquid bridges provided is determined by a formula $a_n \times b_n$, wherein $a_n$ is the number of wells in the first array and $b_n$ is the number of wells in the second array.

The invention also provides a system for mixing samples, the system including, a first gas-free sampling device that interacts with a first sample array, a second gas-free sampling device that interacts with a second sample array, and at least one liquid bridge for mixing the first sample array with the second sample array, wherein the number of liquid bridges provided is determined by a formula $a_n \times b_n$, wherein $a_n$ is the number of wells in the first array and $b_n$ is the number of wells in the second array.

The system can further include robotics to move the first and second sampling devices to interact with the first and second arrays of samples, pumps for acquiring samples in the first and second arrays, a computer operably connected to the system, and a thermocycler.

BRIEF DESCRIPTION OF THE DRAWINGS

FIG. 14 is a further characteristic plot for a liquid bridge segmentor.

FIG. 15 is a photograph of a funicular bridge, also showing dimension parameters.

DETAILED DESCRIPTION

An aspect of the invention provides methods for constructing a liquid bridge system having a predetermined number of liquid bridges sufficient to combine multiple sample arrays for analysis. In its simplest form, aspects of the invention are accomplished by ascertaining a number of wells within a first array of samples, and ascertaining a number of wells within a second array of samples. Based on the number of wells in each of the first and second sample array, a formula $a_n \times b_n$ is applied, in which $a_n$ is the number of wells in the first array and $b_n$ is the number of wells in the second array. The output of this formula determines the number of liquid bridges needed to combine a first sample array and a second sample array to obtain the desired number of sample combinations.

As used herein, an array refers to any device capable of holding a sample. An array can be a plate, such as a 96 well microtiter plate or a 384 well microtiter plate. An array can also be a single vessel or a set of vessels. The vessel can be any type of vessel that is suitable for holding a sample. Exemplary vessels include eppendorf tubes, vials, beakers, flasks, centrifuge tubes, capillary tubes, cryogenic vials, bags, channels, cups, or containers. A well refers to a portion of the array that holds a sample, such as a well of a microtiter plate, a well of an eppendorf tube, a well of a beaker, a well of a centrifuge tube, or a well of a bag.

The first and second array of samples can each independently be any chemical or biological species. In certain embodiments, the sample is a gene or gene product from a biological organism. Standard scientific protocols are available for extraction and purification of mRNA and subsequent production of cDNA. In other embodiments, the sample includes PCR reagents. A typical Q-PCR reaction contains: fluorescent double-stranded binding dye, Taq polymerase, deoxynucleotides of type A, C, G, and T, magnesium chloride, forward and reverse primers and subject cDNA, all suspended within an aqueous buffer. Reactants, however, may be assigned into two broad groups: universal and reaction specific. Universal reactants are those common to every Q-PCR reaction, and include: fluorescent double-stranded binding dye, Taq polymerase, deoxynucleotides A, C, G and T, and magnesium chloride. Reaction specific reactants include the forward and reverse primers and patient cDNA.

Figure 4:
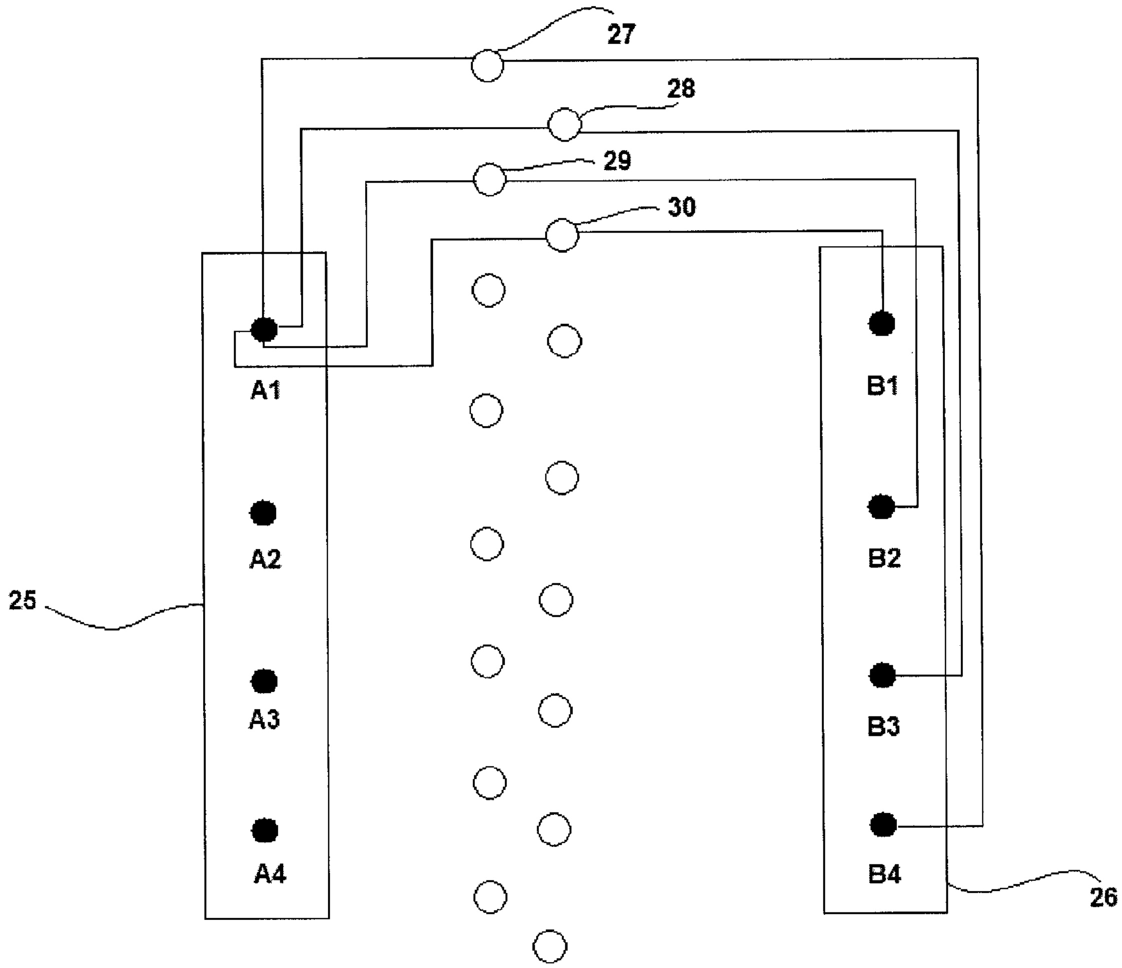
FIG. 4 is a schematic diagram depicting an exemplary liquid bridge system constructed according to the methods of the invention.

FIG. 4 shows a schematic diagram of an exemplary liquid bridge system constructed according to the methods of the invention. First sample array 25 contains four sample wells A1-A4 and second sample array 26 contains four sample wells B1-B4. Based on the number of wells in the first sample array 25 and the number of wells in the second sample array 26, a liquid bridge system is constructed having a number of liquid bridges sufficient to combine the first sample array and the second sample array for analysis. In the embodiment shown in FIG. 4, a system is constructed having 16 liquid bridges, thus providing a system with the capacity to form the required number of sample combinations from a first sample array having four wells and a second sample array having four wells. Samples of the first and second arrays are acquired with sampling devices, such as those shown in Davies et al. (U.S. nonprovisional patent application Ser. No. 12/468,367, filed May 19, 2009, and titled "Sampling Devices", the contents of which are incorporated by reference herein in their entirety).

For simplicity, FIG. 4 is limited to showing combinations of sample A1 from the first sample array 25 with samples B1-B4 of the second sample array 26. Sample A1 is mixed with sample B1 at liquid bridge 27, sample A1 is mixed with sample B2 at liquid bridge 28, sample A1 is mixed with sample B3 at liquid bridge 29, and sample A1 is mixed with sample B4 at liquid bridge 30. Thus in any pair of positions of the first and second sample arrays, all combinations of samples from the first array are mixed with samples from the second array.

Figure 5:
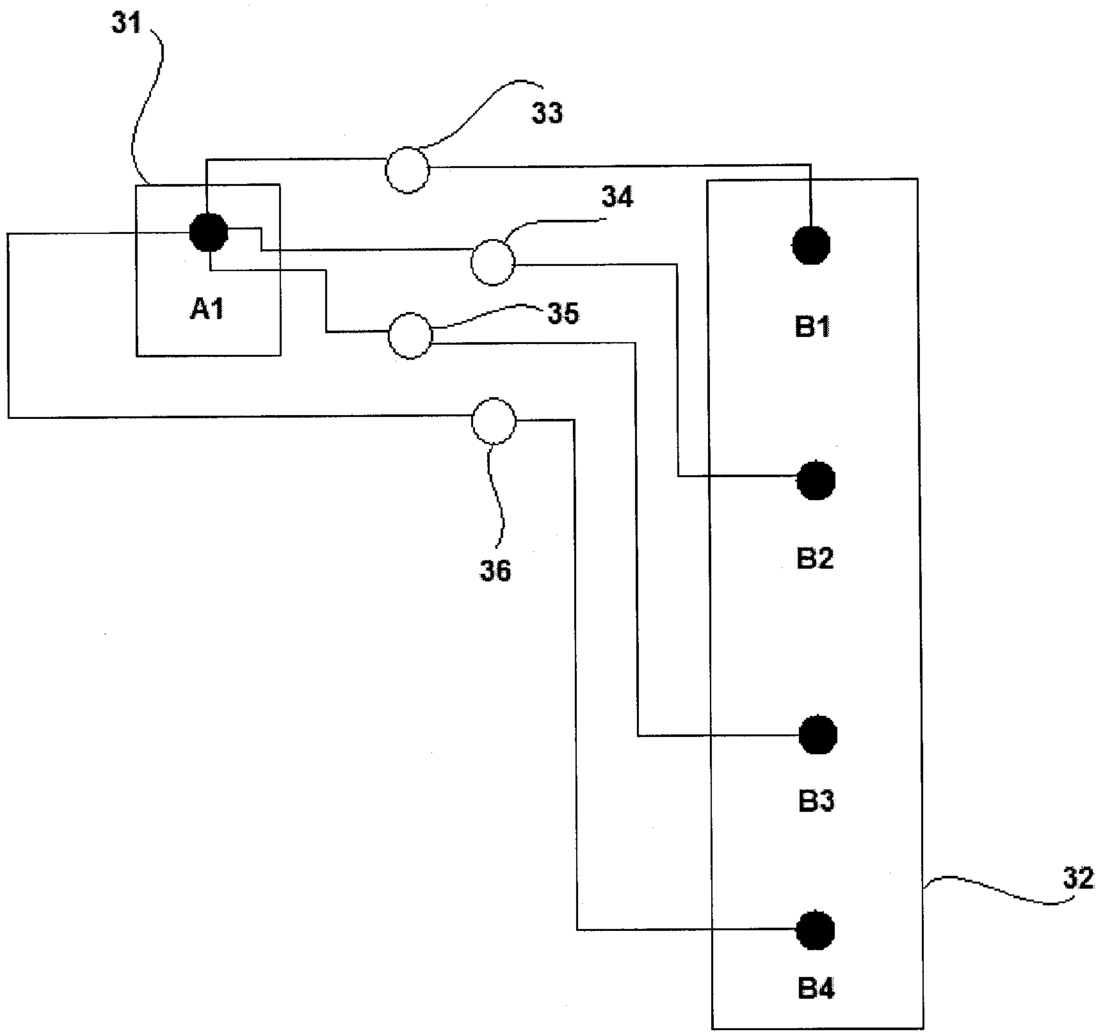
FIG. 5 is a schematic diagram depicting another exemplary liquid bridge system constructed according to the methods of the invention.

FIG. 5 is a schematic diagram depicting another exemplary liquid bridge system constructed according to the methods of the invention. First array 31 contains one sample well A1 and second array 32 contains four sample wells B1-B4. Based on the number of wells in the first sample array 31 and the number of wells in the second sample array 32, a liquid bridge system is constructed with 4 liquid bridges. A system having 4 liquid bridges has the capacity to form the required number of sample combinations from a first sample array having one well and a second sample array having four wells. Samples of the first and second arrays are acquired with sampling devices, such as those shown in Davies et al. (U.S. nonprovisional patent application Ser. No. 12/468,367, filed May 19, 2009, and titled "Sampling Devices").

FIG. 5 shows combinations of sample A1 from the first sample array 31 with samples B1 through B4 of the second sample array 32. Sample A1 is mixed with sample B1 at liquid bridge 33, sample A1 is mixed with sample B2 at liquid bridge 34, sample A1 is mixed with sample B3 at liquid bridge 35, and sample A1 is mixed with sample B4 at liquid bridge 36. Thus in any pair of positions of the first and second sample arrays, all combinations of samples from the first array are mixed with samples from the second array.

Sampling devices can be traversed over arrays of any size, for example, 96 well plates or 384 well plates, to give the desired combinations of samples from the first array with samples from the second array. Methods of the invention can be used to construct a liquid bridge system of any size. Additional exemplary constructed liquid bridge systems include: a first array having two wells, a second array having two wells, and a system having four liquid bridges; a first array having six wells, a second array having six wells, and a system having 36 liquid bridges; a first array having eight wells, a second array having eight wells, and a system having 64 liquid bridges; a first array having 10 wells, a second array having 10 wells, and a system having 100 liquid bridges; or a first array having 12 wells, a second array having 12 wells, and a system having 144 liquid bridges, etc.

Figure 6:
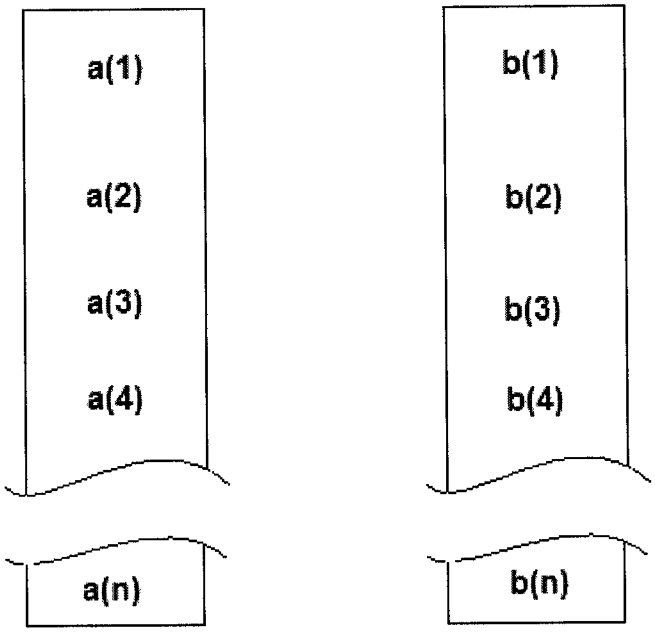
FIG. 6 is a schematic diagram depicting a matrix for forming sample combinations.

A matrix can be used to describe the combinations formed in a general case of mixing a first sample array with a second sample array, as shown in FIG. 6. Contents of wells of the first sample array are represented by (a), and contents of the wells of the second sample array are represented by (b). Mixing combinations are described as follows:

$$a_1 + b_1, a_2 + b_2, \ldots a_1 + b_n$$

$$a_2 + b_1, a_2 + b_2, \ldots a_2 + b_n$$

$$\vdots$$

$$\vdots$$

$$\vdots$$

$$\vdots$$

$$\vdots$$

$$a_n + b_1, a_2 + b_2, \ldots a_n + b_n$$

Thus the combinations required by the instrument user may therefore be specified as a matrix. Further, not all of the wells of each array are required to be filled with a sample. For example, at least one of the sample combinations can be a combination of a blank from the first array and a blank from the second array. An exemplary blank is oil, e.g., silicone oil. By utilizing blanks, the number of assays need not be equal to the number of samples. Further, the system preserves samples by making combinations of blanks (0+0), as opposed to making combinations of a sample and a blank (a+0) or (b+0).

Mixing of samples from the first array with samples from the second array is accomplished using liquid bridges. Exemplary liquid bridges are shown in Davies et al. (WO 2007/091228, the contents of which are incorporated by reference herein in their entirety). In certain embodiments, a liquid bridge includes a chamber having at least one inlet and at least one outlet. The chamber can include as many inlets and outlets as are desired, for example, one inlet and one outlet, two inlets and two outlets, three inlets and three outlets, four inlets and four outlets, one inlet and two outlets, one inlet and three outlets, one inlet and four outlets, two inlets and one outlet, etc.

The chamber and the inlets and outlets can be composed of any inert material that does not interact with the sample or the carrier fluid. Exemplary materials include polytetrafluoroethylene (PTFE; commercially available from Dupont, Wilmington, Del.), polyetheretherketone (PEEK; commercially available from TexLoc, Fort Worth, Tex.), perfluoroalkoxy (PFA; commercially available from TexLoc, Fort Worth, Tex.), or Fluorinated ethylene propylene (FEP; commercially available from TexLoc, Fort Worth, Tex.).

The chamber is configured to receive a carrier fluid, the carrier fluid filling a space in the chamber between the inlet and the outlet. The carrier fluid is immiscible with the sample. In embodiments in which the sample is hydrophilic, an exemplary carrier fluid is an oil, for example silicone oil. In certain embodiments, the silicone oil is PD5 oil. In other embodiments, the oil is any oil that contains a phenol group. Alternatively, the sample can be hydrophobic and exemplary carrier fluids include water or alcohol such as methanol or ethanol.

In certain embodiments, the carrier fluid is density matched with the sample such that a neutrally buoyant environment is produced within the chamber. In embodiments in which the carrier fluid is an oil, the oil typically provides a pressure of no more than 0.5 to 1.0 bar above atmospheric pressure. The oil generally has a viscosity of about 0.08 Pas to about 0.1 Pas.

The inlets and outlets can be of any shape, for example, circular, rectangular, triangular, or square. The inlets and outlets can have an inner diameter ranging from about 10 μm to about 3 mm. For example, the inlets an outlets have an inner diameter of about 10 μm, about 50 μm, about 100 μm, about 150 μm, about 200 μm, about 400 μm, about 600 μm, about 900 μm, about 1 mm, about 2 mm, or about 3 mm. In certain embodiments, the inlets and outlets have the same inner diameter. In other embodiments, the inlets and outlets have different inner diameters. In certain embodiments, each of the inlets have different inner diameters. In certain embodiments, each of the outlets have different inner diameters.

Figure 1:
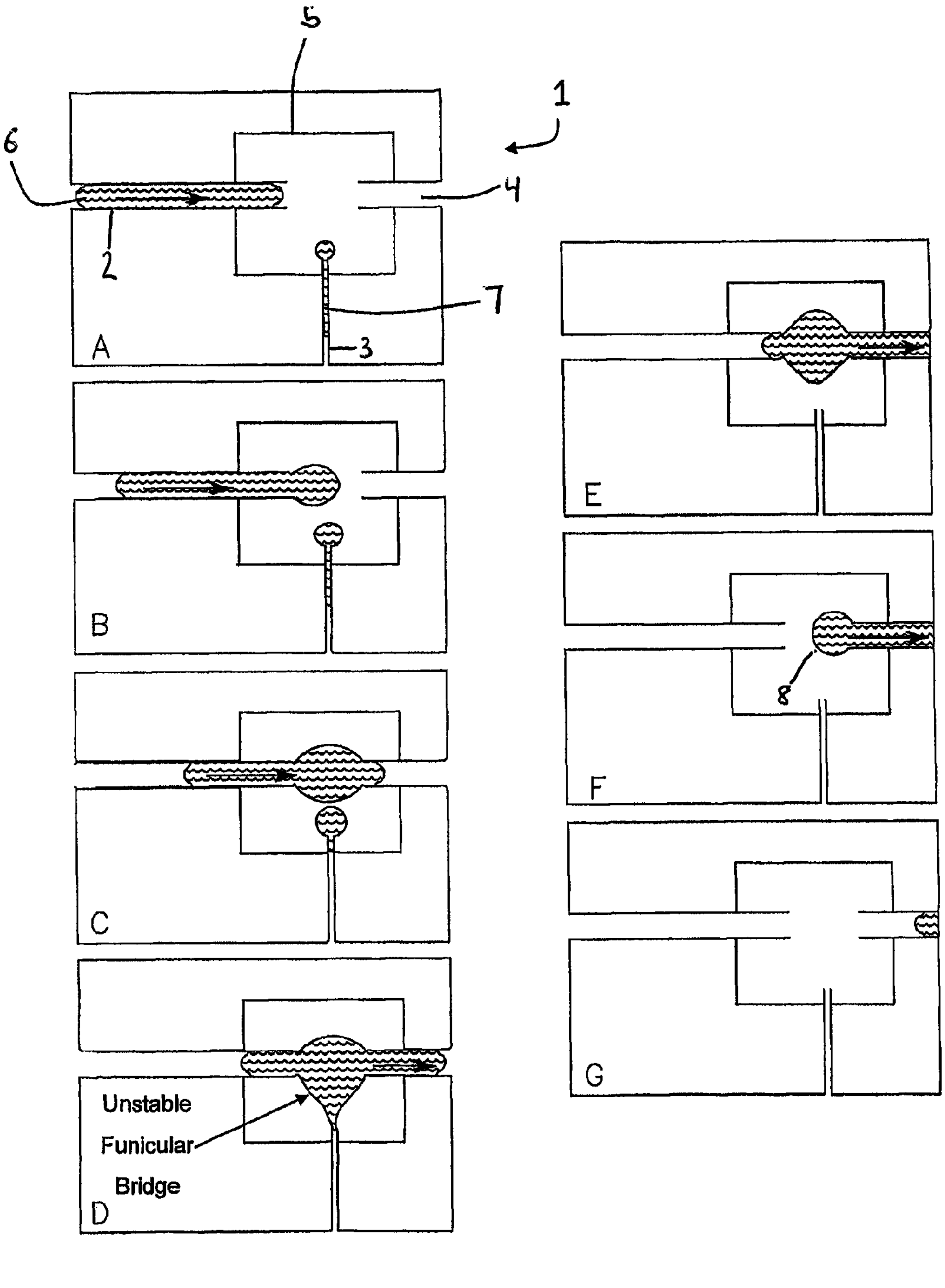
FIG. 1 is a drawing depicting an exemplary embodiment of a liquid bridge having two inlets and one outlet.

The inlet(s) and outlet(s) have dimensions and are positioned in the chamber such that a sample periodically bridges from the inlet(s) to the outlet(s), and droplets of the sample are periodically delivered to the outlet(s). FIG. 1 shows an exemplary embodiment of a liquid bridge having two inlets and one outlet. Referring to FIG. 1 panel A, a bridge 1 includes a first inlet 2, a narrower second inlet 3, an outlet 4, and a chamber 5. The chamber is filled with a carrier fluid, e.g., silicone oil, and the carrier fluid is density-matched with the first sample 6 such that a neutrally buoyant environment is created within the chamber 5. The oil within the chamber is continuously replenished by the oil separating formed droplets of sample. Replenishment of the oil separating the formed droplets results in the droplets assuming a stable capillary-suspended spherical form upon entering the chamber 5.

FIG. 1 panels B and C show that the spherical shape of the sample grows until large enough to span the gap between the ports, forming an axisymmetric liquid bridge. FIG. 1 panel D shows that introduction of a second sample droplet 7 from the second inlet 3 results in formation of an unstable funicular bridge. FIG. 1 panel E shows that the unstable funicular bridge quickly ruptures from the second inlet 3, and the first and second sample droplets combine at the liquid bridge 1. FIG. 1 panels F and G show that upon combination with the first sample 6 and the second sample 7, the droplet 8 containing each of the first sample 6 and the second sample 7 ruptures from the first inlet 2 and enters the outlet 4.

In further detail, the first inlet 2 and the outlet 3 are of diameter 200 μm. The separation of the inlet 2 and the outlet 4 is about 1 mm. The second inlet 3 is of diameter 100 μm, and the distance between the second inlet 3 and the axis of the inlet 2 and the outlet 4 is 1.5 mm. The chamber 5 is 5 mm in diameter and 3 mm in depth. The carrier fluid, e.g., oil provides a pressure of no more than 0.5 to 1.0 bar above atmospheric, and has a viscosity of 0.08 to 0.1 Pas. The flow rate of the samples 6 and 7 entering chamber 5 is in the range of 2 μl/min to 5 μl/min. The carrier fluid is density-matched with each of samples 6 and 7 such that a neutrally buoyant environment is created within the chamber 5.

The pressure in the chamber 5 is atmospheric. The interfacial tension within the chamber 5 is important for effective mixing of samples 6 and 7. Also, the relative viscosity between the samples and carrier fluid is important. The internal pressure (Laplace pressure) within each droplet is inversely proportional to the droplet radius. Thus there is a higher internal pressure within the droplet at the second inlet 3. Because sample 6 and sample 7 are of the same phase, there is little interfacial tension between the droplets of these fluids. Thus, the internal pressures cause a joining of the droplets, akin to injection of one into the other. Also, physical control of the locations of the sample droplets 6 and 7 is achieved by the carrier fluid, which is immiscible with the droplets. In certain embodiments, a surfactant can be added to either the samples 6 and 7 or the carrier fluid to change the interfacial tension.

Figure 2:
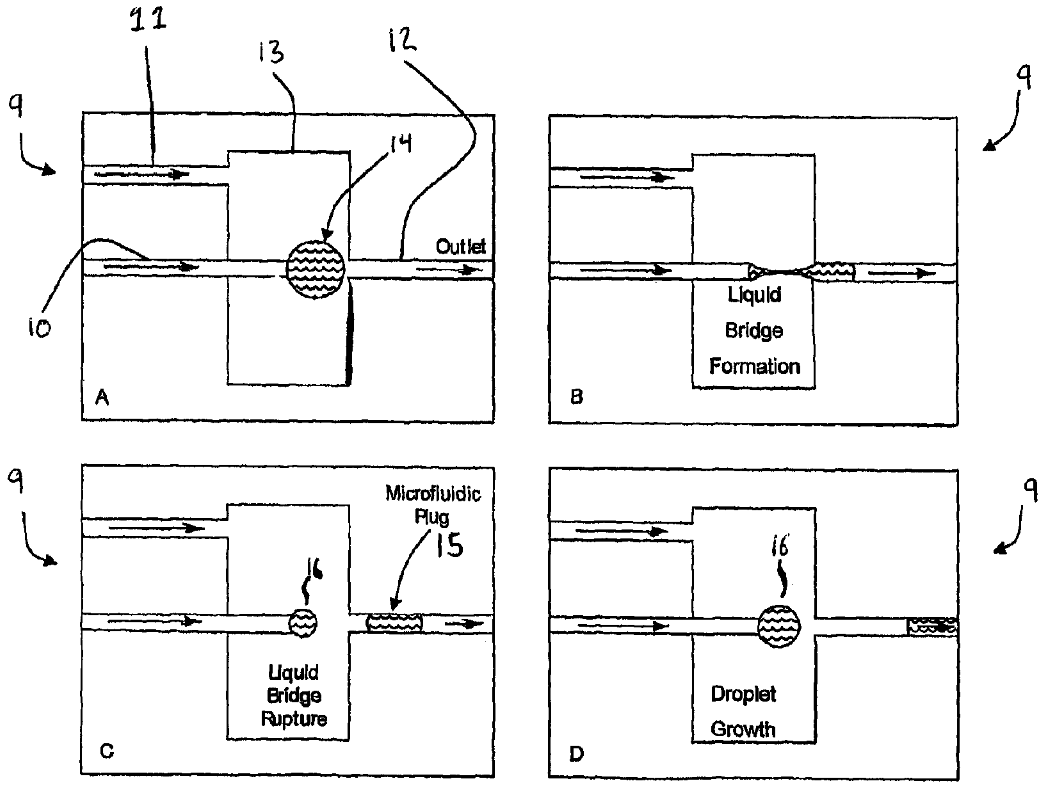
FIG. 2 is a drawing depicting another exemplary embodiment of a liquid bridge having two inlets and one outlet.

FIG. 2 shows another exemplary embodiment of a liquid bridge having two inlets and one outlet. Referring to FIG. 2 panel A, liquid bridge 9 includes a first inlet 10, a second inlet 11, an outlet 12, and a chamber 13. The chamber 13 is filled with a carrier fluid, e.g., silicone oil. The chamber 13 is 5 mm in diameter and 3 mm in depth, and the internal pressure caused by flow of carrier fluid, e.g., silicone oil, from the second inlet 11 into the chamber 13 is no more than 0.5 bar to 1.0 bar above atmospheric pressure. The diameter of the inlets 10 and 11 and outlet 12 is 200 μm. The spacing between the first inlet 10 and the outlet 12 is 0.5 mm. The spacing between these ports can range from 0.2 mm to 1.5 mm. The flow rate of the sample from the inlet 10 into the chamber 13 is 5 μl/min. The flow rate can generally range from about 2 μl/min to about 8 μl/min.

The geometry between liquid bridge 9, and the carrier fluid create a periodic instability between the inlet 10 and the outlet 12 due to surface tension. FIG. 2 panel A shows that an sample droplet 14 is initially formed at the end of the inlet 10. As shown in FIG. 2 panel B, the sample droplet 14 momentarily bridges between the inlet 10 and the outlet 12. The volume held in this bridge is then steadily reduced by the action of pumping carrier fluid into the chamber through the second inlet port 11. FIG. 2, panels B and C show that pumping carrier fluid into the chamber while the sample droplet 14 momentarily bridges between the inlet port 10 and the outlet port 12 results in the formation of an unstable liquid bridge that ruptures to release a microfluidic plug 15 of sample that enters the outlet 12. FIG. 2 panel D shows that subsequent to rupture of the microfluidic plug 15, the process repeats itself with the formation of another sample droplet 16 at the end of inlet 10.

When the flow rate of the carrier fluid entering the chamber 13 from inlet port 12 is substantially the same as the flow rate of sample entering the chamber 13 from the inlet port 10, smaller segmented droplets, separated by the same volume of carrier fluid, e.g., silicone oil, are produced by the bridge 9. The segmenting mechanism reliably produces uniform aqueous microfluidic plugs separated by carrier fluid that do not rely on the shear force exerted by the carrier fluid.

Figure 3:
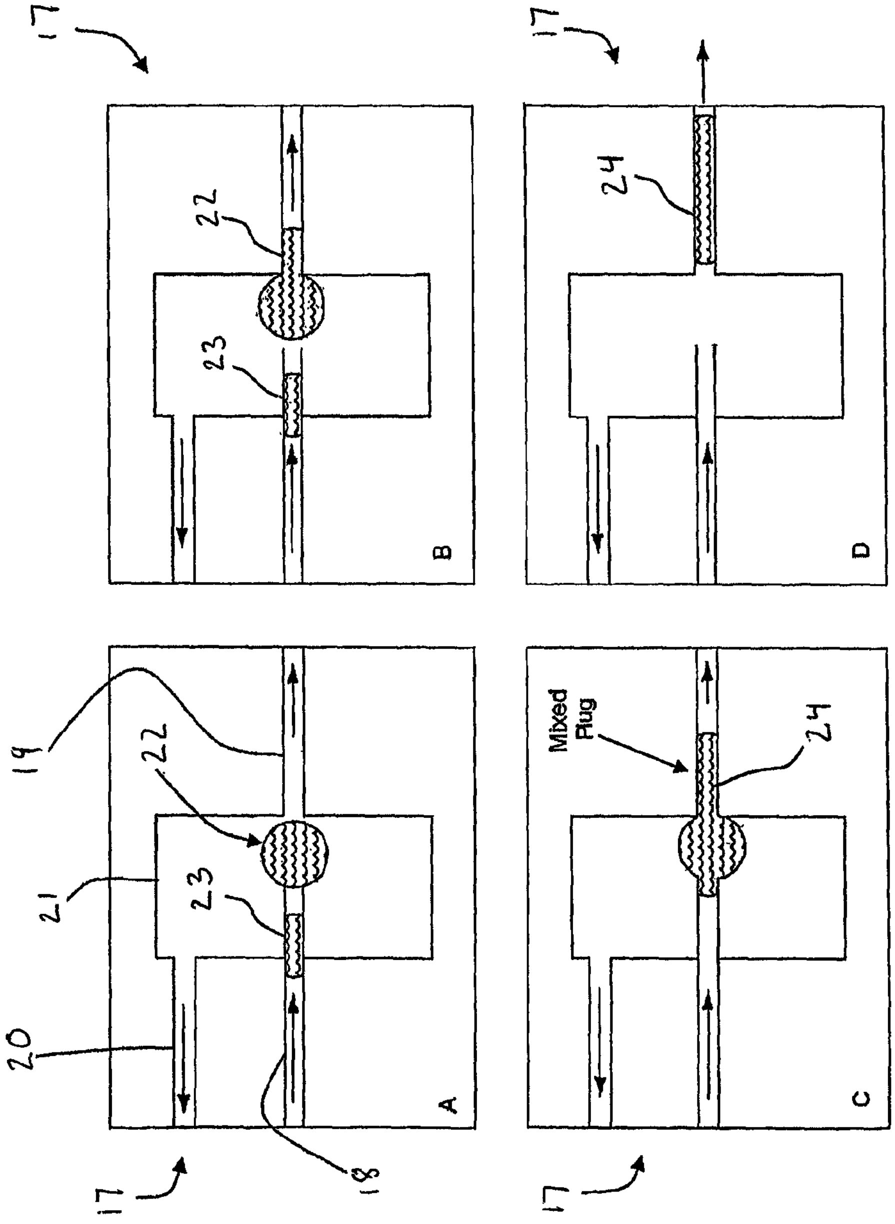
FIG. 3 is a drawing depicting an exemplary embodiment of a liquid bridge having one inlet and two outlets.

In another embodiment, mixing of sample droplets may be achieved using a configuration in which a chamber includes one inlet and two outlets. Sample droplets entering the chamber through the inlet are close together, and the delay for droplet formation within the chamber due to a reduction in fluid flow through a main line results in a collision and hence mixing. Such mixing may be caused by withdrawal of oil from the chamber, or upstream of it. Referring to FIG. 3, a liquid bridge 17 has an inlet 18, a first outlet 19, a second outlet 20, and a chamber 21. The chamber is filled with carrier fluid, e.g., oil, that is immiscible with the sample. A leading droplet of sample entering the chamber 21 through the inlet 18 forms a sample droplet 22 in the chamber at the end of the inlet 18. FIG. 3 panels B and C show that as carrier fluid, e.g., oil, is withdrawn from the chamber 21 through the second outlet 20, a smaller trailing sample droplet 23 collides with the leading sample droplet 22 so that the mixing occurs. FIG. 3 panel D shows a larger mixed sample droplet 24 leaving the chamber 21 via the first outlet 19.

In more detail, initially, the entire system is primed with a density matched carrier fluid, e.g., oil. The diameter of the inlet 18 and the outlets 19 and 20 is 250 μm. The spacing between the inlet 18 and the outlet 19 is about 1 mm. The spacing between the inlet and outlet can range from 0.2 mm to 1.5 mm. The carrier fluid is controlled to have a pressure of about 0.5 bar to about 1.0 bar above atmospheric. The carrier fluid, e.g., silicone oil, has a viscosity of 0.08 to 0.1 Pas.

As with liquid bridges 1 and 9, sample droplets are enveloped by carrier fluid entering and exiting the bridge 17 via a protective film of the carrier fluid firm around the sample droplets. This provides a non-contacting solid surface that prevents carryover contamination from one sample droplet to the next sample droplet. The carrier fluid is used as the control fluid and is density-matched with the sample plugs such that a neutrally buoyant environment is created within the chamber. When two unmixed sample droplets arrive at the chamber in series from the inlet 18, the first droplet assumes a stable capillary-suspended spherical form upon entering the chamber (FIG. 3, panel A). The spherical shape grows until large enough to span the gap between the ports, forming an axisymmetric liquid bridge (FIG. 3, panel B). The second outlet 20 removes a flow of carrier fluid, e.g., oil, from the chamber causing the first sample droplet to slow and remain as a spherical shape at the first outlet 19. This allows time for a second sample droplet to form a stable capillary-suspended spherical shape on entering the chamber 21. With the first sample droplet formed as a spherical shape at the outlet 19, and the second droplet formed as a spherical shape at the inlet 18, the first and second sample droplets can form as one and create an axisymmetric liquid bridge (FIG. 3, panel C). The mixed droplet then exits through the outlet port 19 (FIG. 3, panel D).

In certain embodiments, the flow conditions should be adjusted such that flow through the inlet 18 is greater than the flow through the second outlet 20. A typical flow through the inlet port 18 is about 5 μl/min, and can generally range from about 2 μl/min to about 7 μl/min. The flow away from the chamber 21 through the second outlet 20 is typically 2.5 μl/min and can generally range from about 1 μl/min to about 5 μl/min. Since there is conservation of mass flow within the bridge, this means that the flow through the first outlet 19 will balance the bridge to give a flow of typically 2.5 μl/min, and can generally range from about 1 μl/min to about 5 μl/min.

In certain embodiments, the liquid bridge 17 can be used with a constant outlet flow rate through the second outlet 20. In this embodiment, droplets can be mixed and the fluid flow through the system can be decreased. In addition, liquid bridge 17 can be used in conjunction with a sensor to time the withdrawal of fluid through the second outlet 20 so as to maintain a generally constant sample flow rate.

The sensor used can be a droplet detection sensor that includes a LED and photodiode. The LED is projected directly onto the center of the tube. A photodiode is positioned directly opposite the LED to pick up the light refracted through the tube. As a sample droplet having varying properties compared to that of the carrier fluid, e.g., oil, flows past the LED and photodiode, the light refracted through the liquid is altered slightly. This slight alteration is detected by the photodiode in the form of a change in voltage. This change in voltage can be used to time the control flow through second outlet port 20.

Liquid bridge systems of the invention can further include at least one robotics system to control the gas-free sampling devices. The robotics systems control movement of the sampling device between wells of the first and second arrays and also control sample acquisition. At least one pump is connected to the sampling device. An exemplary pump is shown in Davies et al. (WO 2007/091229, the contents of which are incorporated by reference herein in their entirety). Other commercially available pumps can also be used. The pumps are controlled by a flow controller, e.g., a PC running WinPumpControl software (Open Cage Software, Inc., Huntington, N.Y.), for control of direction of flow and flow rates.

Liquid bridge systems can be fluidly connected, e.g., tubes or channels, to an type of analysis device. In certain embodiments, the liquid bridge system is connected to a thermocycler to perform PCR reactions on the acquired sample. An exemplary thermocycler and methods of fluidly connecting a thermocycler to a liquid bridge system are shown in Davies et al. (WO 2005/023427, WO 2007/091230, and WO 2008/038259, the contents of each of which is incorporated by reference herein in its entirety). The thermocycler can be connected to an optical detecting device to detect the products of the PCR reaction. An optical detecting device and methods for connecting the device to the thermocycler are shown in Davies et al. (WO 2007/091230 and WO 2008/038259, the contents of each of which is incorporated by reference herein in its entirety).

The invention having now been described, it is further illustrated by the following examples and claims, which are illustrative and are not meant to be further limiting. Those skilled in the art will recognize or be able to ascertain using no more than routine experimentation, numerous equivalents to the specific procedures described herein. Such equivalents are within the scope of the present invention and claims.

The contents of all references and citations, including issued patents, published patent applications, and journal articles cited throughout this application, are hereby incorporated by reference in their entireties for all purposes.

EXAMPLES

Example 1

Rupturing of a Sample in a Liquid Bridge

Figure 7:
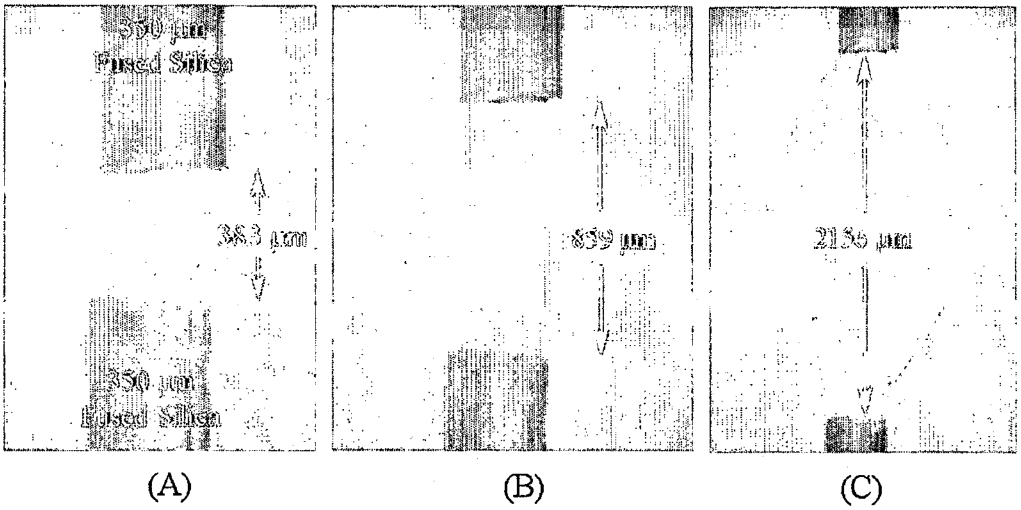
FIG. 7 is a sequence of photographs showing liquid dynamics and dimensions at a liquid bridge.

Liquid bridge stability was studied as a means to predicting the geometric conditions at which rupture occurs. Liquid bridge rupture may be defined as the complete breakage of the liquid filament connecting one solid support to the other. The dimensionless parameters characterizing liquid bridges are used to define the stability boundary at which rupture was observed. FIG. 7 presents images of liquid bridges at three slenderness conditions just prior to rupture. The rupture was caused by the withdrawal of liquid bridge fluid from one capillary tube. It was observed that low slenderness ratio liquid bridges, an example of which is shown in FIG. 7, panel A, adopt a thimble shape at the minimum volume stability. Larger slenderness ratio liquid bridges, such as that shown in FIG. 7, panel C, possess a barrel form with a maximum radius at the bridge mid-span. Intermediate slenderness ratios were found to have a near cylindrical shape at the minimum volume stability limit. FIG. 7, panels A-C show liquid bridges with slenderness ratios of 1.09, 2.45 and 6.16 respectively.

Example 2

Stability of a Liquid Bridge with Respect to Slenderness and Volume

The stability of liquid bridges was examined as a function of slenderness, $\Lambda^*$, which is the ratio of tip separation, L, to the mean diameter, $2R_0$, of the supporting capillaries, i.e. $\Lambda^*=L/2R_0$. Stability was also investigated as a function of volumetric ratio, $V^*$, which is the ratio of liquid bridge volume to the volume of a cylinder with a radius $R_0$, the average radius of the supporting capillaries, i.e.:

$$V^*=\overline{V}/(\pi R_0^2 L).$$

Figure 10:
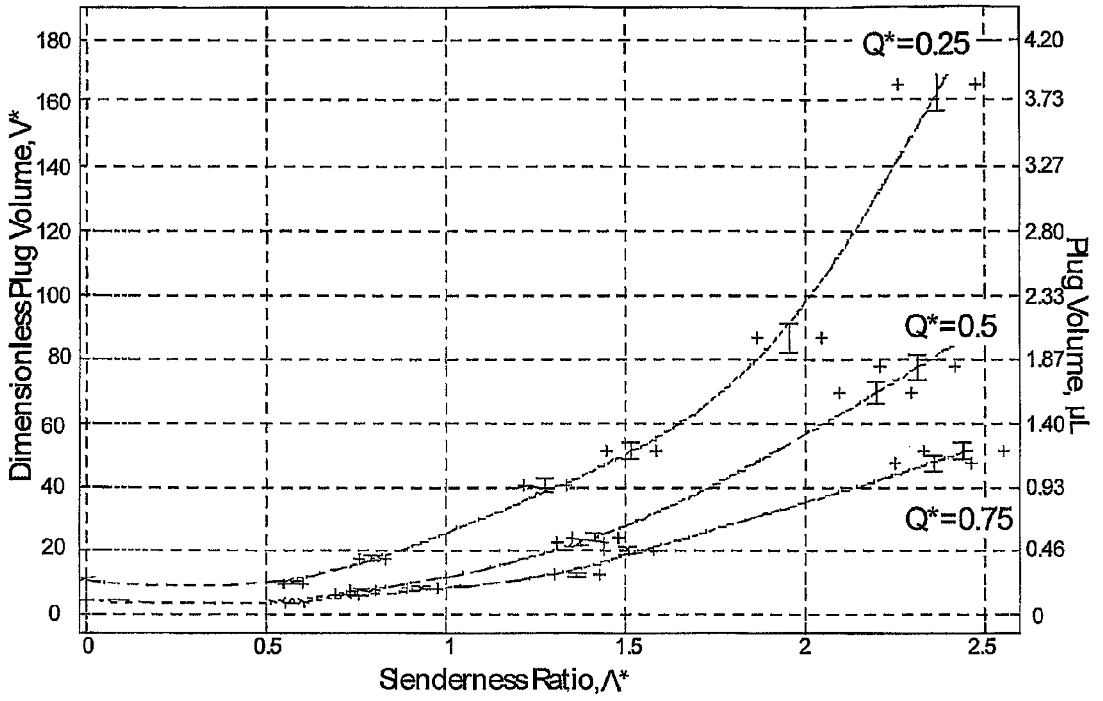
FIG. 10 is a characteristic plot for a liquid bridge segmentor.

The location of the stability boundary, or rupture point, was determined experimentally by fixing the slenderness, establishing a stable liquid bridge between capillary tips and withdrawing fluid from one capillary until rupture was observed. A digital image of the liquid bridge just prior to rupture was then analyzed, using an edge detection measurement technique to determine the total volume and hence the volumetric ratio, $V^*$. The slenderness was then adjusted and the experiment repeated. $K^*$ represents the ratio of the radius of the smaller disk, $R_1$, to the radius of the larger one, $R_2$, that is $K^*=R_1/R_2$. FIG. 10 shows the approximate location of the minimum volume stability boundary for liquid bridges with a lateral Bond number of $1.25\times10^{-4}$, a near weightless environment. Vertical and horizontal error bars indicate experimental uncertainty.

Figure 8:
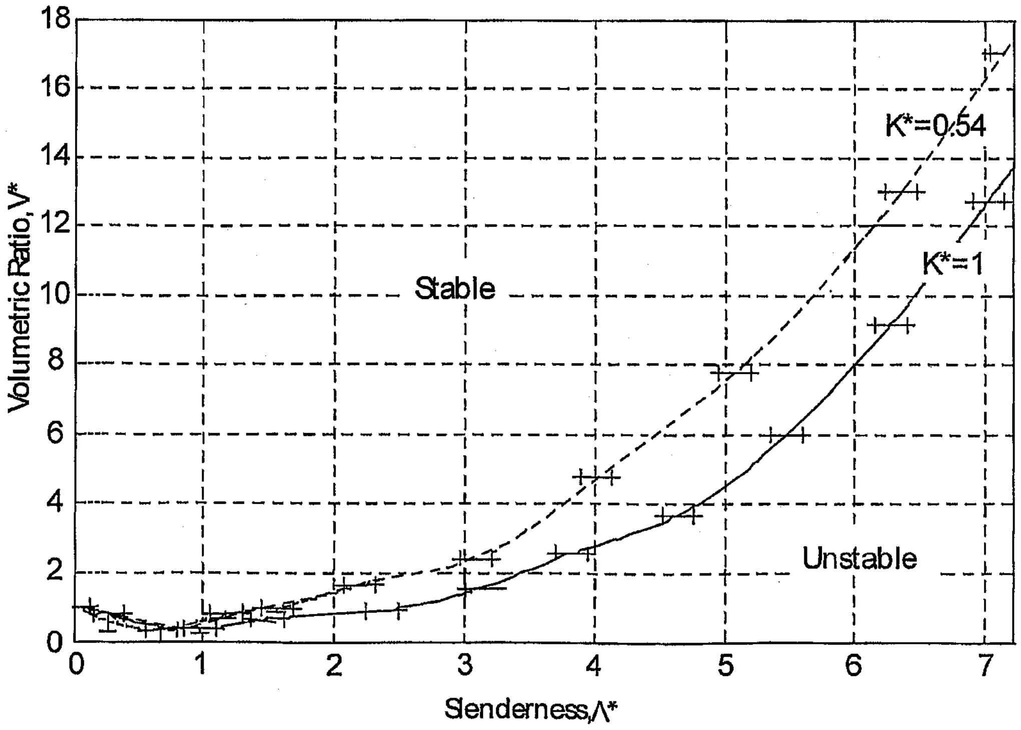
FIG. 8 is a diagram showing a characteristic plot of volumetric ratio vs. slenderness at a liquid bridge for segmentation.

At high volumetric ratios, FIG. 7 panel C for example, bridges maintain their integrity and reach a minimum energy configuration. At low volumetric ratios, FIG. 7 panel A for example, the bridges break before the interfacial energy is minimized. The initial dip in the stability boundary at low slenderness ratios was caused by low-volume droplets not fully wetting the exposed fused silica of the capillary tips. The influence of unequal capillaries on the $\Lambda^*$-$V^*$ stability diagram is also shown in FIG. 8. It can be seen that the unstable region of the $\Lambda^*$-$V^*$ plane increases as the parameter $K^*$, the ratio of capillary radii, decreases. The results presented in FIG. 8 confirmed that the static stability of liquid bridge is purely geometrical at low Bond numbers. It is notable that low slenderness ratio bridges are almost completely stable, with respect to rupture, for all capillary radii measured.

Rupture was observed only at very low volumetric ratios with the liquid bridge assuming a thimble shape. Liquid bridge instability when applied to fluid dispensing is particularly useful as a replacement for micro-channel shear-based dispensing systems. In more detail, FIG. 8 shows a stability diagram for a de-ionized water liquid bridge in a density matched silicone oil, Bond number: $1.25\times10^{-4}$. Vertical error bars indicate the volumetric ratio uncertainty as a result of camera frame rate. Horizontal error bars indicate slenderness uncertainty due to capillary tip misalignment. The parameter $K^*$ is the ratio of supporting capillary radii.

Example 3

Dispensing sub-microliter volumes

The following describes the use of liquid bridge instability as a mechanism for dispensing sub-microliter volumes of fluid in a continuous manner. The dispensing mechanism provided a reliable means of producing uniform aqueous plugs separated by silicone oil that did not rely on the shear force exerted by the carrier fluid. The repeatability with which the method dispensed plugs was examined. The approach used the liquid bridge's dependence on geometry to create a periodic instability between opposing capillary tips. A stable liquid bridge was first established between aqueous inlet and outlet. The volume held in this bridge was then steadily reduced by the action of the silicone oil inlet. This caused the formation of an unstable liquid bridge that ruptured to release a smaller plug at the outlet. The segmenting mechanism provided a reliable means of producing uniform aqueous plugs separated by silicone oil that did not rely on the shear force exerted by the carrier fluid. Furthermore, a protective oil film was established between the walls of the circular capillaries and the droplet to prevent carry-over contamination.

Figure 9:
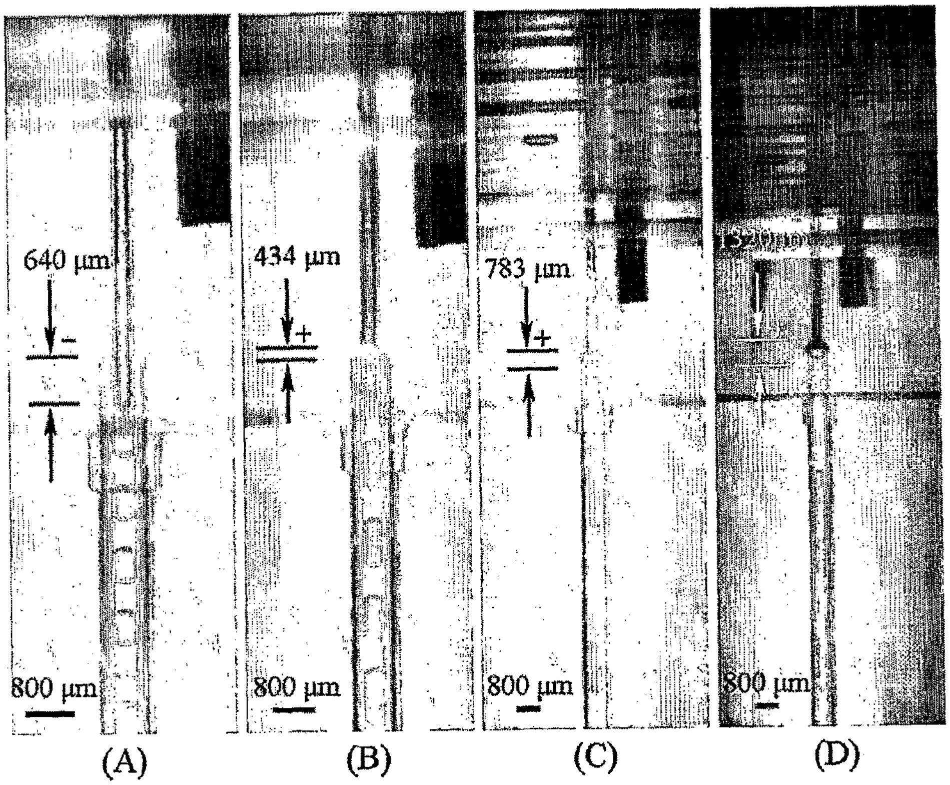
FIG. 9 is a set of photographs of liquid bridge segmentors having different geometries.

FIG. 9 panels A-D shows images of a liquid bridge dispensing at four different slenderness ratios. (A) $\Lambda^*=0$, (B) $\Lambda^*=0.76$, (C) $\Lambda^*=1.37$ and (D) $\Lambda^*=2.31$. $Q^*=0.5$, $K^*=0.44$. Increasing the capillary tip separation, and hence the slenderness ratio increased the plug volumes dispensed. Q*, the oil flow rate as a fraction of the total flow rate, was maintained constant at 0.5. FIG. 9 panel A shows dispensing with the dispensing capillary inserted inside the outlet capillary. This configuration was assigned a slenderness ratio, Λ* of zero. Slenderness ratios close to zero resulted in the smallest volume plugs dispensed for this geometry. The effect of increasing tip separation on dispensed plug volume is shown in FIG. 9 panels B-D. Increasing tip separation, i.e. slenderness ratio, resulted in larger volume aqueous plugs punctuated by approximately the same volume of silicone oil. This was due to the silicone oil inlet flow rate being maintained constant and equal to the aqueous droplet inlet flow rate.

FIG. 10 presents a plot of V*, against slenderness ratio, Λ*, where V* is the dimensionless plug volume scaled with $R_0^3$, i.e.:

$$V^*=\overline{V}/R_0^3.$$

Results are presented for three different values of the oil flow rate fraction, Q*, with the ratio of capillary tip radii, K*, maintained constant at 0.44. The axis on the right-hand side of the plot indicates the measured plug volume. Horizontal error bars indicate slenderness uncertainty as a result of positional inaccuracy. Vertical error bar are a result of uncertainty in the plug volume calculation due to image processing. The results show the expected trend of increased plug volume with liquid bridge slenderness ratio. Decreasing Q* resulted in a dramatic increase in dimensionless plug volume. Altering Q* also affected the volume of silicone oil separating the aqueous plugs as Q* is the oil flow rate as a fraction of the total flow rate. The lowest repeatable volume measured using this particular geometry was approximately 90 mL with $\Lambda^*=0$, $Q^*=0.75$. The highest volume measured was approximately 3.9 μL with $\Lambda^*=2.36$, $Q^*=0.25$.

In flows where the non-wetting fluid, i.e. the aqueous phase, was displaced by wetting fluid, i.e. oil, a thin film of the wetting fluid separated the droplets from the capillary surface. The thickness of the film resulted from a balance between the oil viscosity, η, and the interfacial tension, $\sigma_i$. The thickness of the oil film deposited in a capillary of radius r is given by;

$$h=1.34r(Ca^{2/3}). \quad \text{(Equation (0.1)}$$

The capillary number, Ca, is given by:

$$Ca=\eta U/\sigma_i, \quad \text{(Equation (0.2)}$$

where U represents the mean velocity of the flow. Equation (0.1) is obeyed if the film is thin enough to neglect geometric forces, h<0.1r, and thick enough to avoid the influence of long range molecular attraction, h>100 nm. Typical oil film thicknesses for plug flow through 400 μm polymeric fluorocarbon internal diameter tubing were calculated to be of the order of 1 μm.

This film thickness was too small to resolve with any degree of accuracy from experimental images. However, the oil film did form a protective coating preventing aqueous reactor fluid from contacting the Teflon tubing. This had the advantage of preventing a mechanism responsible for carryover contamination whereby small droplets may be deposited onto the walls of micro-channels. Table 1 below presents two examples of oil-surfactant combinations that were used to successfully establish protective oil films around flowing droplets. Surfactant additives acted to change the interfacial tension between droplets and the oil carrier fluid such as to promote the establishment of a protective oil film, the thickness of which is given by Equation 0.1.

TABLE 1

| Oil | Surfactant | Concentration |
|---|---|---|
| FC40 | 1H,1H,2H,2H-perfluoro-1-decanol | 2% W/V |
| AS100 Silicone Oil | Triton X-100 | 0.1% W/W in PCR Buffer Solution |

Figure 11:
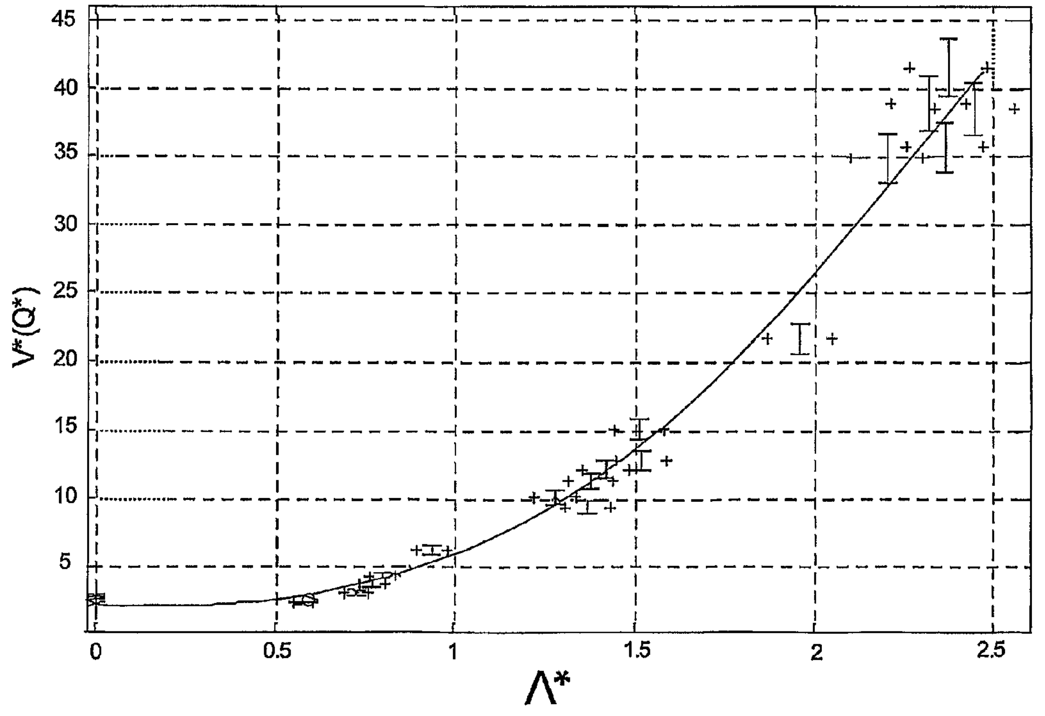
FIG. 11 is a collapsed data characteristic plot for liquid bridge segmentation.

FIG. 11 presents a dimensionless plot of the product of V* and Q* versus Λ*. The data, taken from the plot shown in FIG. 10, collapsed on to the trend line within the bounds of uncertainty. The data applied to geometries with $K^*=0.44$. Notwithstanding this geometric constraint, the collapsed data did yield valuable design information.

Consider a microfiuidic system designer deciding on an appropriate geometry for a segmenting device. The designer will usually know the exact volume to dispense from the outline specification for the device. If there is a sample frequency requirement, the designer may also know a value for Q*. Recalling that $K^*=R_1/R_2$, where $R_1$ and $R_2$ are the inlet and outlet diameters respectively makes the design process relatively easy. Deciding on an arbitrary value for an outlet diameter fixes the aqueous inlet diameter as the data shown in FIG. 12 applies to only to geometries with $K^*=0.44$. With this information in hand, an appropriate value for V*(Q*) may be calculated. The corresponding value for Λ* may then be read from the design curve shown in FIG. 11. Finally, Λ* was used to calculate the tip separation between the inlet and outlet.

Example 4

Droplet Volume with Respect to Liquid Bridges

Figure 13:
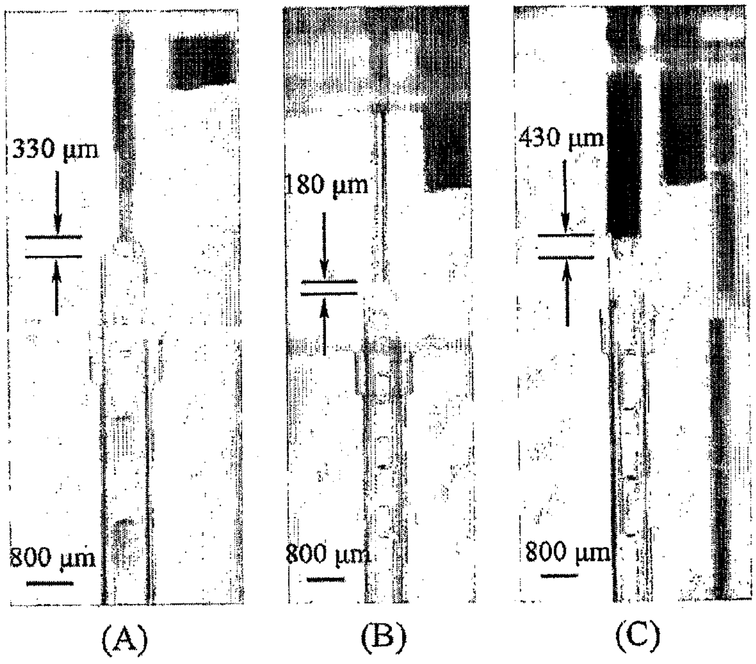
FIG. 13 is a set of photographs of three liquid bridge segmentors having different capillary radii.

The data presented in FIGS. 10 and 11 applied to geometries with $K^*=0.44$. The effect of altering K* on plug volumes dispensed was also investigated. FIG. 13 panels A-C shows a liquid bridge dispensing at three different values for K*. Panels (A), (B) and (C) correspond to K* values of 0.25, 0.44 and 1.0 respectively. K* value of 0.25 was achieved by assembling a 200 μm fused silica microcapillary at the end of a polymeric capillary tube by a reduction of internal diameter through appropriately sized fused silica. Sealing was ensured with the addition of cyanoacrylate glue at the sleeve interfaces.

Figure 12:
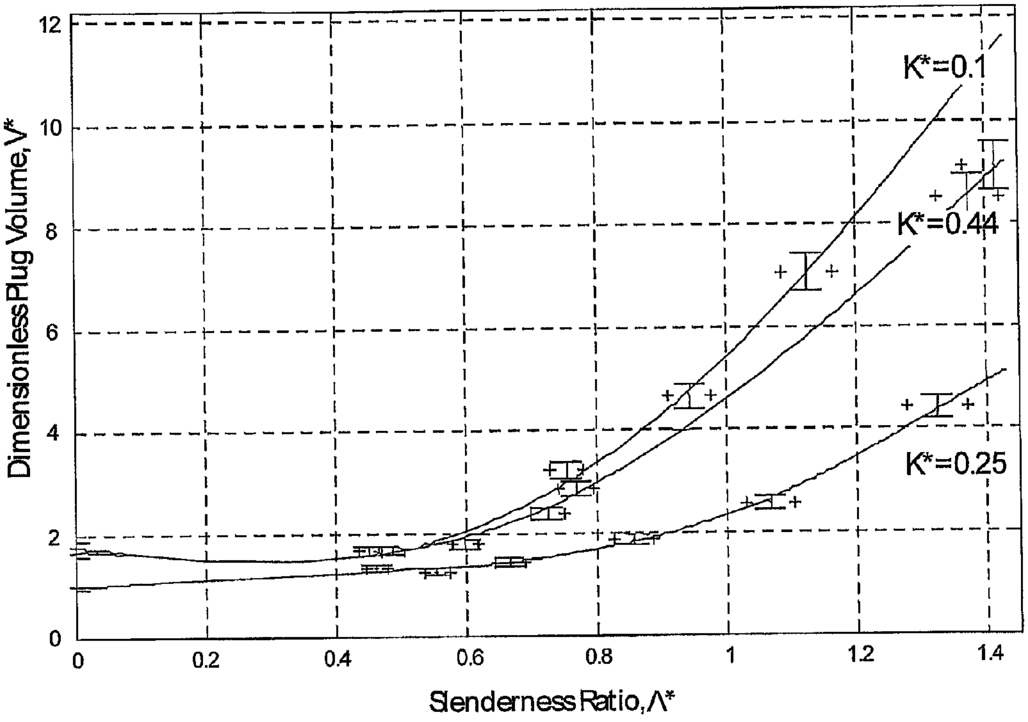
FIG. 12 is a further characteristic plot for a liquid bridge segmentor.

FIG. 12 presents a dimensionless plot of V* versus Λ* for three different values of K*. The dimensionless plug volume, V*, was scaled with $R_2^3$, and not $R_0^3$ as previously. This permitted a direct comparison of dimensionless plug volumes as $R_2$ remained constant throughout the experiment. It was observed that decreasing K* generally lowered the plug volumes dispensed for any given value of slenderness, Λ*. The minimum volume dispensed with K*=0.25 was approximately 60 nL whilst that of K*=0.44 and K*=1 was approximately 110 nL. Attempts to collapse the data shown in FIG. 12 onto a single line, similar to the plot shown in FIG. 11, were unsuccessful. This was due to the highly non-linear relationship between K* and V* for any given value of Λ*.

Example 5

Repeatability of Dispensing Sub-Microliter Volumes

The repeatability with which the liquid bridge dispensing system could deliver fluid was of particular interest. FIG. 14 plots plug volume variation over fourteen measurements for a dispensing system with K*=0.44. The results show mean plug volumes of approximately 120 nL and 56 nL with maximum volumetric variations of ±4.46% and ±3.53% respectively. These volumetric variations compared favorably to commercial available micropipettes that have an uncertainty of ±12% when dispensing 200 nL. The accuracy with which one may dispense using micropipettes, however, is thought to be largely dependant upon user skill. The automation of dispensing systems may therefore be justified as a means of eliminating user-user variability. The volumetric analysis presented in FIG. 14 shows liquid bridge dispensing to be a very repeatable means of continuously dispensing sub-microliter volumes of fluid.

FIG. 15 is an image of a liquid bridge. The bridge consisted of two opposing capillaries of the same external diameter. The second inlet part was of a finer capillary orientated at right angles to and situated half-way between the other two capillaries. Constraints on opposing capillary radius and the placement of the third capillary helped to simplify the dimensionless stability study. The investigation also necessitated modifications to the dimensionless parameters characterizing axisymmetric liquid bridge geometry. The slenderness ratio, Λ*, was calculated using:

$$\Lambda^* = \frac{\sqrt{L^2 + S^2}}{2R_0}, \quad \text{Equation (1)}$$

where L and S correspond to the distances indicated in FIG. 15. $R_0$ is defined as the mean radius, i.e. $(R_1+R_2)/2$. K* is defined as $R_1/R_2$. The volumetric ratio, V*, is defined as:

$$V^* = \frac{\bar{V}}{\pi R_0^2 \sqrt{L^2 + S^2}}, \quad \text{Equation (2)}$$

where $\bar{V}$ is the measured volume at which bridge collapse occurs. In terms of the geometry presented in FIG. 15, a funicular bridge collapse corresponded to detachment from the finer capillary.

Figure 16:
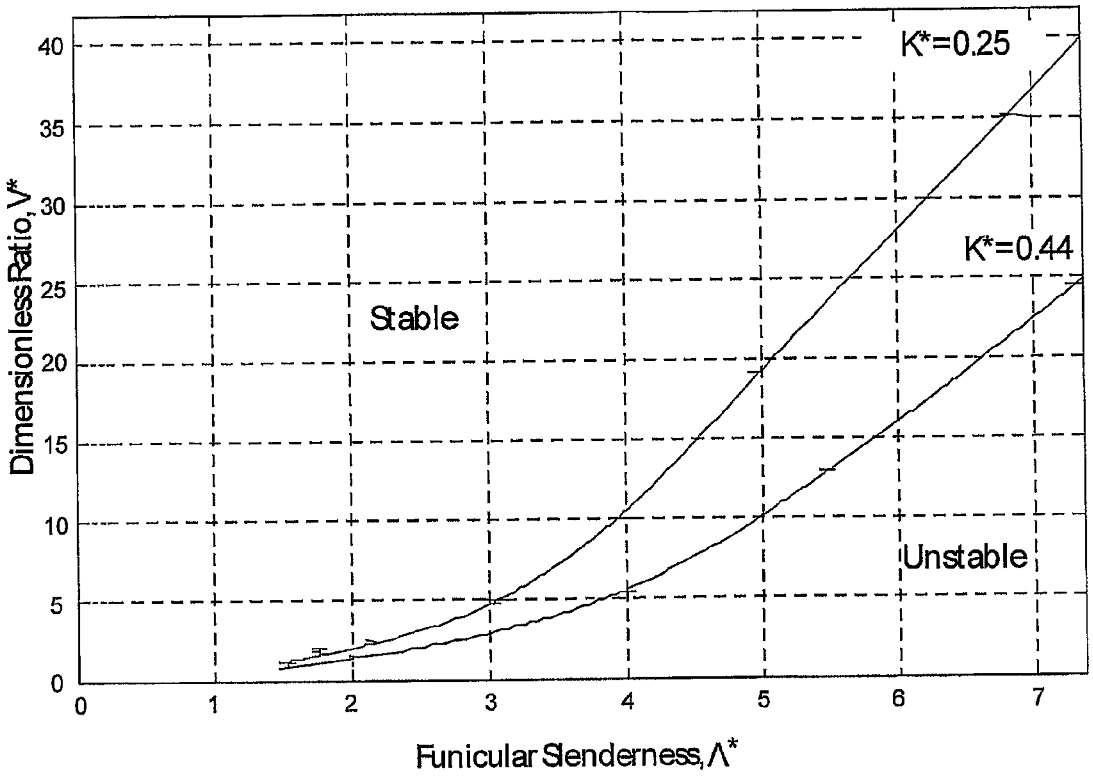
FIG. 16 is a funicular liquid bridge characteristic stability plot.

FIG. 16 shows a stability diagram for the approximate location of the minimum volume stability boundary for purified water funicular liquid bridges with a lateral Bond number of $1.25 \times 10^{-4}$, a near weightless environment. The boundaries of stability were found by fixing a value for Λ*, establishing a stable funicular bridge and withdrawing fluid until the bridge collapsed. The collapse was recorded via a CCD and the frame immediately following rupture was analyzed to measure the volume. The calculation of the bridge volume was simplified by the fact that the collapsed funicular bridge exhibited axisymmetry with respect to the axis of the two larger capillaries. Minimum volume stability boundaries were plotted for K*=0.25 and K*=0.44. Lower K* values displayed increased instability. Volumetric data for Λ* values lower than approximately 1.5 were difficult to obtain with the geometry used and so were omitted from the stability diagram.

The formation of a funicular bridge deemed unstable by the graph shown in FIG. 16 ensured the injection of fluid into an aqueous plug passing through opposing capillaries. A further advantage to using funicular bridge dispensers is based on the speed at which the process takes place. Typical instabilities last of the order of 100 ms, insufficient time for the host droplet fluid to diffuse to the dispensing capillary tip. This is a further preventative measure against carryover contamination.

The two input one output, funicular bridge can be configured so that the expression profile of many genes may be addressed. One input contains the primer and premix in a continuous phase, the outlet then delivers them in droplet form. Firstly many input and output capillaries, say p, can be set in planes perpendicular to that of FIG. 1. A perpendicular arrangement allows for good optical access in the planar thermocycler which is connected to the output. Each arrangement of two inputs and one output can be used to address a single primer, giving p primers. This, however, would make for a very long device in the plane perpendicular to FIG. 1. If serially variant primers were fed into each input, numbering q, this would reduce the scale. Further, if the primers were multiplexed, to order r, in each droplet the scale would be further reduced. The number of primers that could then be addressed would be: N=p×q×r. By this means, a PCR test of the whole genome of any living form, including the human, could be addressed, which would have applications beyond diagnosis, in many fields of pure and applied science.

What is claimed is:

1. A method of constructing a liquid bridge system comprising
   assembling a liquid bridge system comprising a predetermined number of liquid bridges sufficient to combine a first fluid and a second fluid; wherein the first fluid is supplied by a first inlet and the second fluid is supplied by a second inlet; wherein the first inlet is non-parallel to the second inlet; and wherein one of the first fluid and the second fluid is a sample fluid for analysis and the other of the first fluid and second fluid is a reagent.

2. The method according to claim 1, further comprising ascertaining a number of wells within a first array, and ascertaining a number of wells within a second array; wherein the first fluid is provided by the first array and the second fluid is provided by the second array.

3. The method according to claim 2, further comprising applying a formula $a_n \times b_n$, wherein $a_n$ is the number of wells in the first array and $b_n$ is the number of wells in the second array.

4. The method according to claim 1, wherein the first and second-fluids are each independently chemical or biological species.

5. The method according to claim 1, wherein the first fluid is primers for PCR reactions and the second fluid comprises nucleic acid.

6. The method according to claim 5, wherein the nucleic acid is DNA or cDNA.

7. A liquid bridge system constructed by the process of claim 1.

8. The method according to claim 1, wherein the first fluid, via the first inlet, and the second fluid, via the second inlet, are supplied to and combined at the predetermined number of liquid bridges.

* * * * *